United States Patent [19]

Takenaka et al.

[11] 3,966,823
[45] June 29, 1976

[54] PROCESS FOR PREPARING 1,3-BUTADIENE AND METHACROLEIN SIMULTANEOUSLY

[75] Inventors: Shigeo Takenaka; Hitoshi Shimizu; Kenichiro Yamamoto, all of Takasaki, Japan

[73] Assignee: Nippon Kayaku Kabushiki Kaisha, Tokyo, Japan

[22] Filed: Nov. 1, 1971

[21] Appl. No.: 194,501

[30] Foreign Application Priority Data

Nov. 7, 1970  Japan.............................. 45-97548

[52] U.S. Cl....................... 260/604 R; 260/533 N; 260/533 R; 260/593 R; 260/680 E
[51] Int. Cl.²......................................... C07C 45/04
[58] Field of Search ..................... 260/604 R, 680 E

[56] References Cited
UNITED STATES PATENTS

| | | | |
|---|---|---|---|
| 3,414,631 | 12/1968 | Grasselli et al.................. | 260/680 E |
| 3,642,930 | 2/1972 | Grasselli et al.................. | 260/680 E |

FOREIGN PATENTS OR APPLICATIONS

| | | | |
|---|---|---|---|
| 427,881 | 3/1967 | Japan............................. | 260/604 R |

OTHER PUBLICATIONS

Voge et al., "Catalytic Oxidation of Olefins," pp. 185–191.

*Primary Examiner*—James O. Thomas, Jr.
*Assistant Examiner*—W. B. Lone
*Attorney, Agent, or Firm*—Russell & Nields

[57] ABSTRACT

The present invention relates to a production of 1,3-butadiene and methacrolein simultaneously by catalytic oxidation of mixed butenes composed of butene-1, cis-2-butene, trans-2-butene (unless otherwise mentioned, these three butenes will referred to as n-butenes hereinafter) and iso-butylene more particularly, this invention relates to a process for preparing 1, 3-butadiene and methacrolein simultaneously in high yields by oxidizing the mixed butenes mainly composed of n-butenes and isobutylene with molecular oxygen at an elevated temperature in the presence of a catalyst having the empirical formula:

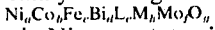

wherein Ni represents nickel, Co represents cobalt, Fe represents iron, Bi represents bismuth, Mo represents molybdenum, O represents oxygen, L represents at least one element selected from the group of phosphorus, arsenic and boron, M represents at least one element selected from the group of potassium, rubidium and cesium, and $a,b,c,d,e,f,g$ and $h$ represent numbers of atoms of Ni, Co, Fe, Bi, L, Mo, O and M, respectively, with the proviso that when $(f)$ is 12, $(a)$ and $(b)$ independently are numbers of 0 – 15, (a)+(b) being 15 – 1, $(c)$ is a number of 7 – 0.5, (d) is a number of 4 – 0.1, (g) is a number of 36 – 98 which is accounted from typical oxides of these metals, (e) is a number of 0 – 4 and (h) is a number of 0.01 – 1.0. According to the present invention, the final products, i.e. 1.3 - butadiene and methacrolein are produced with a high selectivety from said mixed butenes without excessive oxidation of the olefins to undesired higher oxidation products of carbon such as carbon monoxide, carbon dioxide, maleic acid and acetic acid.

5 Claims, No Drawings

PROCESS FOR PREPARING 1,3-BUTADIENE AND METHACROLEIN SIMULTANEOUSLY

BACKGROUND OF THE INVENTION

The oxidation of a single composition of n-butenes or isobutylene to a corresponding oxide have been known.

A process for preparing only 1,3-butadiene with catalyst similar to this invention is previously disclosed in Japanese Pat. Publication No. 26842/1968. For preparing methacrolein, a similar catalysts is used in Japanese Pat. Publication No. 2324/1968. The catalysts used in said Patent are composed of, for example, nickel, cobalt, iron, bismuth, phosphorus and molybdenum. The highest single pass yields in Examples given in the specification is 83% for single pass yield of 1,3-butadiene from butene-1, and is only 37% for those of methacrolein.

On the other hand, a process for the simultaneous preparation of methacrolein and 1,3-butadiene in the same method as in the present invention have been also disclosed in Japanese Pat. Publication No. 7881/1967. In the specification of this publication, the same process carried out over a catalyst comprised of oxides of V, Bi and Mo, and the highest yields of 67% for methacrolein, but that of only 76% for 1,3-butadiene are obtained.

DETAILED DESCRIPTION

The difference between the catalysts used in the present invention and those of Japanese Pat. Publication Nos. 26842/1968 and 2324/1968 is the existence of a small amount of said potassium, rubidium or cesium which improve the selectivities of the catalysts to methacrolein and 1,3-butadiene.

According to the process of the present invention, the highest single pass yield of 1,3-butadiene from n-butenes under the proper operating conditions amounts to 90 – 91% and that of methacrolein from isobutylene amounts to about 72%.

Prior to the oxidation of the single component of either n-butenes or iso-butylene, a purified single component of butene should be prepared by means of a physical or chemical separation of isobutylene from n-butenes. At present, industrial sources for butenes are provided from $C_4$ fractions formed in petroleum naphtha cracking and residue obtained by extracting out 1,3-butadiene from the $C_4$ fractions. This residue, however, still contains four butenes, (i.e. isomers of butene-1, cis-2-butene, trans-2-butene and isobutylene) which are quite similar to each other in both physical and chemical properties and, therefore, separation and purification of a desired component are not easy and thus single component of butenes is too expensive to be used as industrial starting material.

The products obtained by the process of the present invention are mainly composed of 1,3-butadiene and methacrolein with a boiling points of 4°C and 68°C, respectively and, therefore, the separation of these products can be done easily by a simple physical operation.

When the mixture of different butenes is used as starting materials, the four butenes are generally different from each other in reactivity, the order being, isobutylene>butene-1>cis-2-butene>trans-2-butene. In the presence of the catalyst according to the present invention, the optimum reaction temperature of at least the main components, n-butenes, particularly, butene-1 and isobutylene is nearly the same (about 340°–370°C). Difference in reaction temperature between them is recognized to be at most about 2°C. This is an great advantageous that nearly the same temperature can be preferred in the simultaneous reaction to obtain same conversions. It means that no limitation is made in mixing ratio of starting olefins and that the mixture of said two butenes in any proportion can be used. This is also advantageous in a reaction wherein starting materials are circulated, and this is quite significant from industrial viewpoint.

The catalyst useful in the process of the present invention is composed from mixture, compound or complex made up of the oxides of nickel and/or cobalt, iron, bismuth, molydbenum, elements represented by L and M. The composition is conveniently expressed in the empirical formula mentioned above.

Of the above compositions, suitable preferred catalysts are obtained, when $(f)$ is 12, $(a)$ is 0 – 5, $(b)$ is 1 – 12, $(a) + (b)$ is 4 – 12, $(c)$ is 1 – 5, $(d)$ is 1 – 3, $(e)$ is 0 – 2, $(g)$ is 45 – 60 and $(h)$ is 0.01 – 1.0.

And moreover, more suitable ones are obtained, when $(f)$ is 12, $(a)$ is 0 – 2, $(b)$ is 3 – 12, $(a) + (b)$ is 4 – 12, $(c)$ is 1 – 4, $(d)$ is 1 – 3, $(e)$ is 0 – 1, $(g)$ is 45 – 60 and $(h)$ is 0.01 – 0.5.

The catalyst of this invention is usually prepared by adding aqueous solutions of the suitable-water soluble salt of nickel and/or cobalt, iron, bismuth and at least one single acid selected from the group consisting of phosphoric, arsenic and boric to another aqueous solution of ammonium molbydate mixed with the solution of potassium nitrate, rubidium nitrate or cesium nitrate. The resulting slurry is then mixed with a carrier such as silica gel, silica sol, diatomaceous earth, Carborundum or α-alumina. Silica sol is particularly preferred. The foregoing mixture is heated, if desired, to remove water and dry to be a solid cake. The solid cake is then calcined at an elevated temperature of 500°– 800°C in the air, for a period longer than four hours.

The catalyst of this invention is preferably calcined at high temperature for reducing production of undesired oxides such as carbon dioxide, and particularly it is recommended that the following catalyst is calcined at temperature of from 650° – 800°C;

$(a)$ is 0, $(b)$ is 1 – 15, $(c)$ is 1 – 5, $(d)$ is 1 – 3, $(e)$ is 0 – 2, $(f)$ is 12, $(g)$ is 45 – 60 and $(h)$ is 0.01 – 0.1

The catalyst is suitable for use in some physical forms such as grains or pellets. The catalyst of this invention may be used in a fixed bed reactor, in a fluidized bed or in a moving bed.

As molecular oxygen, air is useful in general. Oxygen alone or a mixture of it with an inert gas such as nitrogen or carbon dioxide which have no effect in this reaction may be also useful for this reaction. The catalytic oxidation process of this invention can be carried out at a temperature of from 250° – 450°C and under a pressure of from 0.5 to 10 atmospheres absolute in the presence of steam. In the oxidation with air and steam, the contact time of feed gas which is measured in a real temperature and pressure is usually from 0.5 to 10 seconds and preferably from 1 to 8 seconds at atmospheric pressure. The oxidation of the process embodied herein requires the presence of from 0.5 to 4.0 preferably 1.6 to 2.8 mols of oxygen and the presence of from 1 to 20, preferably, 2 to 6 mols of water, per one mol of total butenes fed.

The process of this invention will now be described in more detail in regard to the specific desired products, namely, methacrolein and 1,3-butadiene. In this present specification to following definitions are employed;

$$\text{Conversion } (c) \% = \frac{\text{Mols of n-butenes or isobutylene converted}}{\text{Mols of n-butenes or isobutylene fed}} \times 100$$

$$\text{Selectivity to 1,3-butadiene } (s) \% = \frac{\text{Mols of 1,3-butadiene obtained}}{\text{Mols of n-butene converted}} \times 100$$

$$\text{Selectivity to Methacrolein } (s) \% = \frac{\text{Mols of methacrolein obtained}}{\text{Mols of isobutylene converted}} \times 100$$

$$\text{Single Pass Yield of 1,3-butadiene or methacrolein } (S.P.Y.) \% = \frac{\text{Mols of 1,3-butadiene or methacrolein obtained}}{\text{Mols of n-butenes or isobutylene fed}} \times 100$$

$$= (s) \times (c)$$

EXAMPLE 1 – 10

63.5 g of ammonium molybdate $(NH_4)_6Mo_7O_{24}\cdot 4H_2O$ were dissolved in distilled water. Into the resulting solution, 1.7 g of orthophosphoric acid and 0.22 g of potassium nitrate were added with heating and stirring. About 90 g of water-soluble silica containing 20% of silica were added therein.

On the other hand, 22.0 g of nickel nitrate $Ni(NO_3)_2\cdot 6H_2O$, 39.4 g of cobalt nitrate $Co(NO_3)_2\cdot 6H_2O$ and 36.6 g of ferric nitrate $Fe(NO_3)_3\cdot 9H_2O$ were dissolved in small quantity of water respectively. 14.6 g of bismuth nitrate $Bi(NO_3)_3\cdot 5H_2O$ was also dissolved in 30 ml of distilled water containing 3.5 ml of conc. nitric acid. Finally, all of solutions above were added with stirring to the foregoing mixture containing silica sol.

The resulting slurry was dried and heated to 200°C. After cooling, the resulting solid was pulverized, pelleted and calcined at 700°C for 6 hours in the air.

Composition of the catalyst thus obtained was represented by the following formula:

$$Ni_{2.5}Co_{4.5}Fe_{3.0}Bi_{1.0}P_{0.5}K_{0.07}Mo_{12}O_{54}$$

About 150 ml of the above catalyst were filled in a SUS 27 reactor tube of inside diameter of 21.6 mm. The reactor tube was then placed in a salt bath of molten potassium maintained at 320° – 350°C. Olefine used as starting materials was composed of 0.485 mol fraction of 1-butene (98.0% of purity, the others was 2-butenes) and 0.515 mol of isobutylene (97.0% of purity, the others was butanes). The gaseous mixtures of olefines, air and steam in the molar ratio of 1 : 76 – 15.2 : 3.0 – 8.0 were passed over the catalyst at the contact time of 2.0 – 3.5 seconds.

The reaction products were analyzed by means of Gas Chromatography and acid-base titration. The main products were in order of their amount, 1,3-butadiene, methacrolein, carbon dioxide, cis- and trans-2-butenes, acetone, carbon monoxide, acetic acid, aldehyde and acrolein. Methacrylic acid was only a small amount. Results with some variation of temperature of niter bath and molar ratio of air and steam to the olefines fed, are given in table 1.

Table 1

| Example No. | Catalyst Composition | Molar ratio of gases fed $C_4H_8:O_2:H_2O$ | Temp. of salt bath (°C) | Contact time (sec) | Conversion (C) % Butene-1 | Conversion (C) % Iso-butylene | Single Pass Yield(S.P.Y.) % 1,3-Butadiene | Single Pass Yield(S.P.Y.) % Methacrolein | Selectivity (S) % 1,3-Butadiene | Selectivity (S) % Methacrolein |
|---|---|---|---|---|---|---|---|---|---|---|
| 1 | $Ni_{2.5}Co_{4.5}$ | 1:2.2:5.0 | 335 | 2.7 | 98.2 | 98.0 | 91.5 | 71.2 | 93.2 | 72.6 |
| 2 | $Fe_{3.0}Bi_{1.0}$ | 1:1.9:5.0 | 331 | 3.1 | 95.5 | 94.3 | 88.3 | 67.7 | 92.5 | 71.8 |
| 3 | $P_{0.5}K_{0.07}$ | 1:3.2:5.0 | 320 | 2.3 | 98.3 | 97.5 | 89.2 | 68.5 | 90.7 | 70.2 |
| 4 | $Mo_{12}O_{54}$ | 1:2.5:6.2 | 321 | 2.6 | 97.5 | 96.2 | 91.2 | 70.3 | 93.6 | 69.6 |
| 5 |  | 1:1.6:6.2 | 345 | 2.9 | 95.0 | 93.8 | 90.3 | 62.1 | 92.7 | 66.2 |
| 6 |  | 1:2.2:6.2 | 280 | 3.5 | 89.3 | 86.2 | 83.8 | 63.5 | 93.8 | 73.6 |
| 7 |  | 1:2.2:5.0 | 360 | 2.4 | 97.6 | 96.8 | 89.3 | 64.8 | 91.5 | 67.0 |
| 8 |  | 1:2.2:5.0 | 380 | 2.0 | 98.5 | 98.8 | 87.1 | 61.3 | 89.0 | 62.0 |
| 9 |  | 1:2.2:3.0 | 340 | 3.0 | 95.2 | 94.0 | 88.5 | 66.8 | 93.0 | 71.0 |
| 10 |  | 1:2.2:8.0 | 340 | 2.3 | 93.5 | 92.2 | 85.0 | 67.8 | 91.0 | 73.6 |
| Comparative Example 1 | $Ni_{2.5}Co_{4.5}$ $F_{3.0}Bi_{1.0}$ $P_{0.5}$ $Mo_{12}O_{54}$ | 1:2.2:6.2 | 315 | 2.5 | 96.0 | 99.8 | 82.5 | 41.2 | 85.9 | 41.3 |

Note: Molar ratio of butene-1 to isobutylene is 1 : 1.16

COMPARATIVE EXAMPLE 1

A catalyst was prepared in the same procedure as the Example 1 - 10 except that potassium was not included in the catalyst composition (that is, h in $M_h$ in the general formula of catalyst is made zero). The reaction condition was nearly as same those of Example 1 - 10. The results of comparative Example 1 are also shown in Table 1.

EXAMPLE 11 – 21.

Table 2 shows some variations of the composition of catalyst prepared by the procedure of Example 1 –10. These were variable number (e) of phosphorus atoms and number (h) of potassium or cesium atoms. Butenes fed was composed of 0.48 mol fraction of butene-1, 0.50 of isobutylene and the others of butanes, which was same to that of Example 1 - 10. Molar ratio of $C_4H_8 : O_2 : H_2O$ was fixed to be 1 : 2.2 : 5.0.

Table 2

| Example No. | Number of elements (e) P | (h) K | CnS | Temp. of salt bath (°C) | Conversions of (C) % butene-1 | isobutylene | Single pass yield of (S.P.Y.) % 1,3-butadiene | methacrolein |
|---|---|---|---|---|---|---|---|---|
| 11 | 1.0 | 0.1 | — | 340 | 95.3 | 94.8 | 88.9 | 67.3 |
| 12 | 1.0 | 0.2 | — | 345 | 95.5 | 97.4 | 87.0 | 66.5 |
| 13 | 1.0 | 0.3 | — | 345 | 94.5 | 96.5 | 84.9 | 64.5 |
| 14 | 0.5 | 0.02 | — | 328 | 96.0 | 99.5 | 82.3 | 63.5 |
| 15 | 0.5 | 0.8 | — | 355 | 95.5 | 92.7 | 85.1 | 60.4 |
| 16 | 3.0 | 0.07 | — | 328 | 96.0 | 98.5 | 84.2 | 62.5 |
| 17 | 0.0 | 0.07 | — | 348 | 96.5 | 97.0 | 87.3 | 69.8 |
| 18 | 0.5 | — | 0.3 | 345 | 95.0 | 94.2 | 86.1 | 65.7 |
| 19 | 0.5 | — | 0.5 | 350 | 95.5 | 93.0 | 84.7 | 62.2 |
| 20 | — | 0.07 | — | 345 | 95.5 | 94.8 | 90.3 | 71.2 |
| 21 | — | 0.1 | — | 348 | 96.3 | 95.8 | 89.5 | 70.3 |

A replacement of $K_{0.3}$ with $Rb_{0.3}$ in Example 13 brought nearly the same results.

EXAMPLE 22 - 25

Table 3 shows the replacement of phosphorus with arsenic in the composition of catalyst prepared like in the Example 1 – 10. Reaction conditions were the same as that of Example 1.

Table 3

| Example No. | Catalyst Compositions (Number of elements) Ni | Co | Fe | Bi | As | K | Mo | Conversions (C) % butene-1 | isobutylene | Single pass yield (S.P.Y.) % 1,3-butadiene | methacrolein |
|---|---|---|---|---|---|---|---|---|---|---|---|
| 22 | 4.5 | 4 | 1 | 1 | 1 | 0.07 | 12 | 94.3 | 94.0 | 88.0 | 61.8 |
| 23 | 4.5 | 4 | 1 | 1 | 0.5 | 0.05 | 12 | 93.2 | 92.7 | 86.2 | 63.9 |
| 24 | 3.0 | 2 | 2 | 1 | 0.5 | 0.1 | 12 | 96.0 | 95.1 | 90.0 | 68.0 |
| 25 | 0 | 7 | 3 | 1 | 0.5 | 0.07 | 12 | 96.5 | 94.8 | 90.8 | 67.5 |

When a catalyst that was prepared by an exchange of $AS_{0.5}$ for $B_{0.5}$ was used in Example 14, nearly the same results as in Example 14 was obtained.

EXAMPLE 26 - 27

The results obtained by the variation of atomic ratio of Ni, Co, Fe for various ratio of Bi were shown in Table 4. Reaction conditions were the same as that of Example 1.

Number of atoms P, K and Mo in the catalyst compositions were fixed to 0.5, 0.07 and 12 respectively, so that the description of these number was cut out in this table.

Table 4

| Example No. | Catalyst Compositions (Number of elements) Ni | Co | Fe | Bi | Conversions (C) % butene-1 | isobutylene | Single pass yield (S.P.Y.) % 1,3-butadiene | methacrolein |
|---|---|---|---|---|---|---|---|---|
| 26 | 0 | 12 | 3 | 1 | 92.5 | 90.5 | 84.8 | 68.2 |
| 27 | 0 | 8 | 5 | 1 | 96.5 | 96.0 | 89.7 | 67.5 |
| 28 | 0 | 4.5 | 3 | 1 | 96.0 | 94.5 | 90.4 | 69.0 |
| 29 | 10 | 1 | 3 | 1 | 96.0 | 95.5 | 85.5 | 61.3 |
| 30 | 5 | 5 | 2 | 1 | 95.5 | 95.0 | 85.7 | 65.5 |
| 31 | 1 | 8 | 3 | 1 | 96.0 | 95.5 | 89.7 | 69.2 |
| 32 | 0 | 8 | 1 | 1 | 94.5 | 92.5 | 85.0 | 64.2 |
| 33 | 2.5 | 5 | 2 | 0.5 | 93.0 | 91.5 | 85.0 | 62.4 |
| 34 | 1 | 5 | 3 | 0.5 | 97.5 | 97.0 | 91.0 | 67.5 |
| 35 | 0 | 7 | 3 | 0.5 | 96.5 | 96.4 | 91.3 | 68.4 |
| 36 | 0 | 8 | 3 | 2 | 96.0 | 95.5 | 90.5 | 69.0 |
| 37 | 0 | 8 | 3 | 3 | 96.5 | 95.0 | 89.7 | 65.5 |

EXAMPLE 38 – 39

In Example 1 - 37, the butenes mixture which was ratio of 1 : 1.16, butene-1 to isobutylene were used.

In Example 38 – 39 various mixtures of butenes, especially, for butene-1 and isobtylene were passed over the same catalyst as prepared in Example 1. Molar ratio of total $C_4H_8$ : $O_2$ : $H_2O$ was 1 : 22 : 5.0.

Table 5

| Example No. | Compositions of butenes as starting material butene-1 | isobutylene | Temp. of salt bath (°C) | Conversions (c) % butene-1 | isobutylene | Single pass yield (S.P.Y.) % 1,3-butadiene | methacrolein |
|---|---|---|---|---|---|---|---|
| 38 | 2 | 1 | 324 | 97.5 | 96.3 | 92.5 | 71.8 |
| 39 | 1 | 2 | 342 | 98.0 | 97.5 | 92.3 | 70.7 |

EXAMPLE 40 – 41

In Table 6, combined mixtures of cis-2-butene or trans-2-butene with isobutylene were used as a starting butene. Molar ratio of total $C_4H_8$ : $O_2$ : $H_2O$ in fed gas was 1 : 2.2 : 5.0, and the compositions of butenes was 1 : 1.6 for cis- or trans-2-butene to isobutylene. The composition of catalyst used was same as that of Example 1.

Table 6

| Example No. | Temp. of salt bath (°C) | Conversions (C) % cis- or trans- 2-butene | isobutylene | Single pass yield (S.P.Y.) % 1,3-butadiene | methacrolein |
|---|---|---|---|---|---|
| 40 | 405 | cis-2-butene 91.5 | 98.2 | 80.5 | 57.0 |
| 41 | 410 | trans-2-butene 88.5 | 99.0 | 76.5 | 52.5 |

EXAMPLE 42 – 44

Conversions and single pass yields obtained by passing a typical spent butanes-butenes fraction (it contains 27.5% of butene-1, 48.1% of isobutylene, 8.6% of trans-2-butene, 5.6% of cis-2-butene and additional about 9.0% of butanes) over the same catalyst as in Example 1 at temperature of 360° – 370°C for contact time 3.2 sec were listed in Example 42 of table 7. Example 43 – 44 shows some variation of total pressure of reaction system. The catalyst of this invention has little or no activity against the butanes contained in reagent gasses fed.

Table 7

| Example No. | Temp. of salt bath (°C) | Press. of reaction system (atm abs) | Conversions (C) % n-butene | isobutylene | Single pass yield (S.P.Y.) % 1,3-butadiene | methacrolein |
|---|---|---|---|---|---|---|
| 42 | 362 | atmospheric | 81.9 | 98.8 | 72.1 | 67.8 |
| 43 | 365 | 2 | 82.5 | 97.3 | 70.5 | 65.9 |
| 44 | 370 | 3 | 81.0 | 96.5 | 69.8 | 62.9 |

We claim:

1. The process for preparing 1,3-butadiene and methacrolein simultaneously by reacting butene mixture containing n-butenes and isobutylene with molecular oxygen in the presence of steam and a catalyst of the empirical formula;

$Ni_aCo_bFe_cBi_dL_eM_hMo_fO_g$ wherein Ni, Co, Fe, Bi, Mo and O are the chemical symbols of the corresponding elements, L represents at least one element selected from the group consisting of phosphorus, arsenic and boron, M represents at least one element selected from the group consisting of potassium, rubidium and cesium, $a$, $b$, $c$, $d$, $e$, $f$, $g$ and $h$ represent number of atoms of Ni, Co, Fe, Bi, L, Mo, O and M, respectively, and (f) is 12, ($a$) and ($b$) independently are numbers of 0–15, (a) + (b) being 1–15, (c) is a number of 0.5–7, (d) is a number of 0.1–4, (g) is a number of 36–98 (e) is a number of 0–4 and (h) is a number of 0.01–1.0, wherein the reaction is carried out at a temperature of from 250°C to 450°C, wherein the molar ratio of oxygen, per one mole of total olefins is 0.5–4:1 and the molar ratio of steam per one mole of total olefins is 1–20:1 and wherein the reaction is carried out under a pressure of 0.5–10 atmospheres absolute.

2. The process of claim 1, wherein (a) is 0 – 5, (b) is 1 – 12, (a) + (b) is 4 – 12, (c) is 1 – 5, (d) is 1 – 3, (e) is 0 – 2, (f) is 12 (g) is 45 – 60 and (h) is 0.01 – 1.0.

3. The process of claim 1, wherein ($a$) is 0 – 2, ($b$) is 3 – 12, ($a$) + ($b$) is 4 – 12, ($c$) is 1 – 4, ($d$) is 1 – 3, ($e$) is 0 – 1, ($f$) is 12, ($g$) is 45 – 60, ($h$) is 0.01 – 0.5.

4. The process of claim 1, wherein the catalyst is incorporated on a silica carrier.

5. The process of claim 1, wherein the following catalyst calcined at temperature of from 650° – 800°C is used;

(a) is 0, (b) is 1 - 15, (c) is 1 - 5, (d) is 1 - 3, (e) is 0 - 2, (f) is 12, (g) is 45 - 60 and (h) is 0.01 - 0.1.

* * * * *